United States Patent [19]
Kim et al.

[11] Patent Number: 5,815,253
[45] Date of Patent: Sep. 29, 1998

[54] METHOD AND APPARATUS FOR ESTIMATING PERFORMANCE OF GAS TUBE

[75] Inventors: Jin-Sung Kim; Taek-Jin Lim, both of Suwon; Gui-Jin Kim, Seoul, all of Rep. of Korea

[73] Assignee: Samsung Electronics Co., Ltd., Suwon, Rep. of Korea

[21] Appl. No.: 760,511

[22] Filed: Dec. 5, 1996

[30] Foreign Application Priority Data

Dec. 6, 1995 [KR] Rep. of Korea ................... 1995 47221

[51] Int. Cl.$^6$ .................................................. G01N 21/88
[52] U.S. Cl. ............................................. 356/72; 356/237
[58] Field of Search ............................ 356/72, 73, 237, 356/241

[56] References Cited

U.S. PATENT DOCUMENTS

| | | | |
|---|---|---|---|
| 4,017,336 | 4/1977 | Foroulis | 148/6.35 |
| 5,375,760 | 12/1994 | Doko | 228/183 |
| 5,456,768 | 10/1995 | Tomari et al. | 148/280 |
| 5,589,148 | 12/1996 | Otsuka et al. | 428/240 S |
| 5,620,854 | 4/1997 | Holzrichter et al. | 435/6 |

*Primary Examiner*—Richard A. Rosenberger
*Attorney, Agent, or Firm*—Jones & Volentine, L.L.P.

[57] ABSTRACT

Method and apparatus for estimating the performance of a gas tube. The method comprising the steps of: (a) preparing a sample tube to be analyzed and cutting the sample tube in a desired size and shape; (b) examining distribution of defects and surface condition of the cut sample tube with an optical microscope; (c) analyzing structure and composition of surface defects which can not be measured in the step (b), to determine type and composition of the surface defects and shape of a surface grain; (d) analyzing structure of an inner surface-treated layer of the sample tube along the thickness thereof; and (e) synthetically analyzing data for defect density and surface roughness, which are numerically expressed through the steps (a) to (d), to define a reference data which can be used in a semiconductor manufacturing process.

6 Claims, 3 Drawing Sheets

METHOD AND APPARATUS FOR ESTIMATING PERFORMANCE OF GAS TUBE

BACKGROUND OF THE INVENTION

1. Field of the Invention

The present invention relates to a method and apparatus for analyzing the performance of a gas tube applied to a delivery system of high purity gases or chemicals in semiconductor manufacturing processes, and more particularly, to a method and apparatus for estimating the performance of a gas tube, which is capable of objectively and synthetically estimating an adverse effect imposed on a gas or chemical delivery system due to contamination of the gas tube.

2. Description of the Related Art

When high purity gas used for a semiconductor manufacturing process is supplied into a reaction chamber where an actual process is implemented, it is very important to supply the gas in a low contamination level state. A gas delivery system includes various elements, such as a regulator, a valve, a mass flow controller (MFC), etc. While performance of these elements is important, the performance of the gas tube is considered to be more important because the contamination of the gas tube imposes a harmful influence on various elements related thereto. For example, when particle contamination is produced in a gas tube for corrosive gas, it has a direct influence on the subsequent filter or the mass flow controller (MFC), deteriorating the performances thereof.

Therefore, a method for effectively estimating the performance of a gas tube has been strongly demanded. However, since the prior art cannot objectively and synthetically estimate the performance of the gas tube, it becomes very difficult to control the semiconductor manufacturing equipments in practice.

Certain methods for estimating the performance of a gas tube according to the prior art will now be described. First, a chemical composition analyzing method analyzes the composition of impurities contained in a raw material which flows through a gas tube and compares the analyzed data with each other. Second, a surface roughness analyzing method measures the roughness of a surface-treated gas tube by a profiler in a lengthwise direction of the gas tube. However, because the surface defects substantially exist along the length of the gas tube, the methods for estimating the performance of a gas tube of the prior art cannot exactly represent the total roughness at a sufficient level.

SUMMARY OF THE INVENTION

Accordingly, the present invention has been made in an effort to solve one or more of the problems occurring in the prior art, and it is an object of the present invention to provide a method and apparatus for estimating the performance of a gas tube, by which the performance of a gas tube is objectively and synthetically estimated, whereby it is possible to precisely analyze an initial state of the gas tube and extract reference data suitable for management of the gas tube.

According to one aspect of the present invention, there is provided a method for estimating the performance of a gas tube, the method comprising the steps of: (a) preparing a gas tube to be analyzed and cutting the gas tube in a desired size and shape to obtain a sample tube; (b) examining distribution of defects and surface condition of the cut sample tube with an optical microscope; (c) analyzing structural and compositional features of surface defects of the cut sample tube which can not be measured in said step (b), to determine type and composition of the surface defects and shape of a surface grain; (d) analyzing structure of an inner surface-treated layer of the sample tube along the thickness thereof; and (e) synthetically analyzing data for defect density and surface roughness, which are numerically expressed through the steps (a) to (d), to define a reference data which can be used in practicing a semiconductor manufacturing process.

According to another aspect of the present invention, the sample tube is made from stainless steel.

According to another aspect of the present invention, the step (c) is implemented using an electron-probe microscopy analyzer.

According to another aspect of the present invention, the step (d) is implemented using an Auger electron spectroscope.

According to another aspect of the present invention, the method further comprises the step of (f) analyzing a surface roughness over a predetermined area for estimating defect density, size and depth of a grain, and surface roughness of another sample tube.

According to still another aspect of the present invention, said step (f) is implemented using an atomic force microscope.

According to yet still another aspect of the present invention, there is provided an atomic force microscope for analyzing surface roughness of a sample tube comprising: a tip contacted with an inner surface of the sample tube to be analyzed; and a tip holder for securely holding the tip; wherein the tip holder has a small outer diameter and a long length such that the tip can approach a center portion of the sample tube for measurement.

By the features of the present invention, the method and apparatus for estimating performance of a gas tube provides certain advantages in that it is possible to objectively analyze the initial state of a gas tube to define reference data which can be used in the practice of a semiconductor manufacturing process.

BRIEF DESCRIPTION OF THE DRAWINGS

The above objects, and other features and advantages of the present invention will become more apparent after a reading of the following detailed description taken in conjunction with the drawings, in which:

FIGS. 3A to 3D are cross-sectional views, each showing points where the actual estimating process is performed, wherein FIG. 3A illustrates estimating points by an optical microscope, FIG. 3B illustrates estimating points by an electron probe microscopy analyzer (EPMA), FIG. 3C illustrates an estimating point by an Auger electron spectroscope (AES) and FIG. 3D illustrates estimating points by an atomic force microscope (AFM);

DETAILED DESCRIPTION OF PREFERRED EMBODIMENTS

Hereinafter, a method and apparatus for estimating the performance of a gas tube will be fully described with reference to the drawings.

Figure 1:
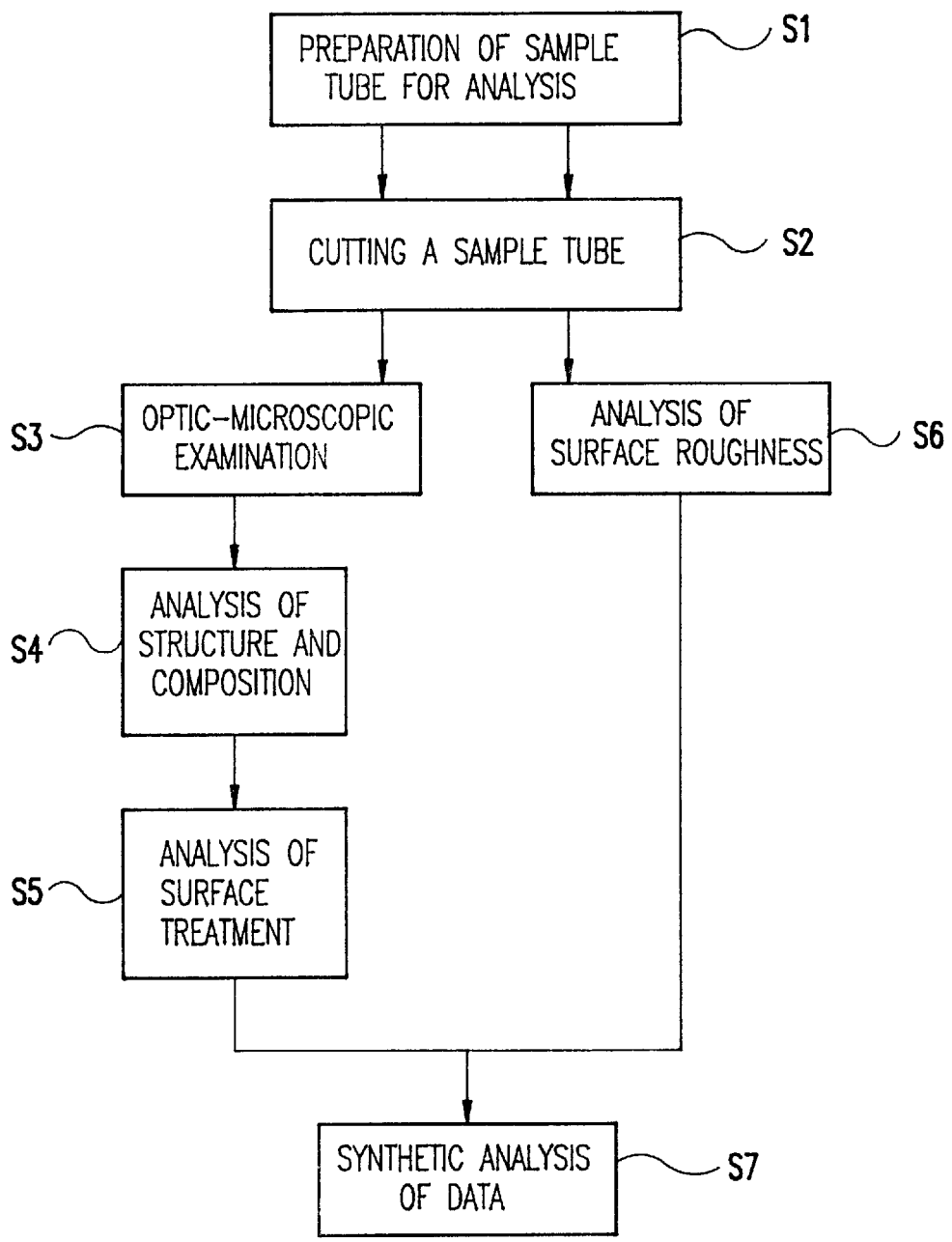
FIG. 1 is a flow chart illustrating the method for estimating the performance of a gas tube, in accordance with an embodiment of the present invention.
Figures 2A, 2B, 2C, 2D:
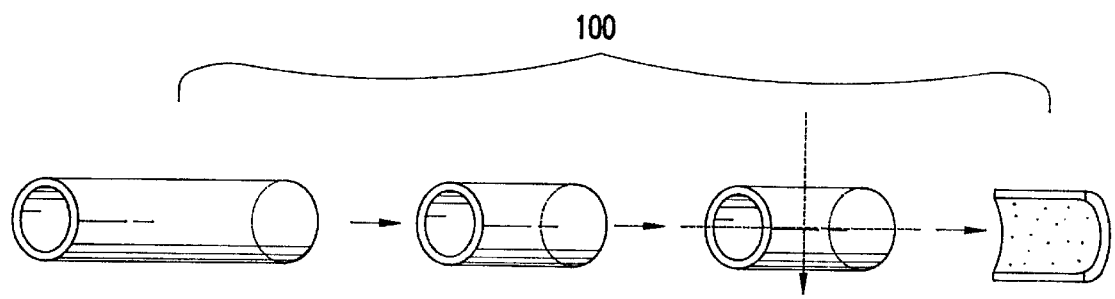
FIGS. 2A to 2D are perspective views showing a process by which a sample tube is prepared.

Referring to FIG. 1, the method for estimating the performance of a gas tube is performed through steps S1–S7. First, in a sample preparing step S1 and cutting step S2, a tube 100 which is made from material such as stainless steel, or the like, and through which a gas or chemical solution has passed, is prepared (see FIG. 2A), and then cut into a proper size suitable for estimation (see FIG. 2B). Then, the tube 100 is cut again into two sample halves (see FIG. 2C) to define a sample tube as shown in FIG. 2D. The sample tube 100 should be cut by a cutter such that the sample tube 100 can uniformly represent the whole sample tube, and particles generated during cutting are removed by nitrogen ($N_2$) gas. Then, the history of the sample tube is recorded, and the sample tube is stored.

Figures 3A, 3B, 3C, 3D:
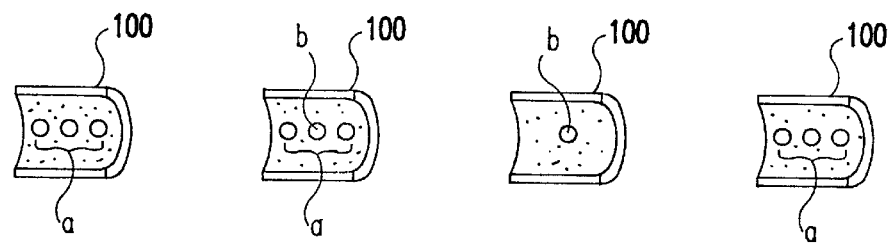

In step S3, the prepared sample tube 100 is examined by an optical microscope. The optical microscope examination in step S3 is used to examine the distribution of defects or surface roughness by using the optical microscope. By varying the magnification of the optical microscope to high or low, photographs of three examination points a are obtained to analyze the density of the defects (see FIG. 3A).

Next, step S4 analyzes the structure and composition of the sample tube 100. More specifically, the structure and composition analyzing step S4 analyzes the structure and composition of surface defects which cannot be measured in step S3 so as to ascertain the types of surface defects and the shapes of surface grains. It is preferable to utilize an electron probe microscopy analyzer (EPMA) for implementing step S4. In implementing step S4, the structural analysis procedure uses a scanning electron microscope (SEM) which photographs three points a of the sample tube 100 to analyze the structure of the surface defects thereby in order to classify the types of the defects in detail and to determine the density of each defect type (see FIG. 3A). Furthermore, the composition analysis procedure uses an X-ray (EDX) which photographs only one point b on the center of the sample tube to predict process abnormalities in practice (see FIG. 3B).

In a surface treatment analyzing step S5, the composition of the inner surface of the sample tube 100 which is electro-polished with a metal oxide layer is measured along the thickness thereof. It is preferable that the surface treatment analyzing step S5 be implemented using an Auger electron spectroscope (AES). In the surface treatment analyzing step S5, only one point b on the center of the sample tube is examined to measure the distribution of the thickness of the surface treated layer to predict the durability of the sample tube (see FIG. 3C).

Although the above steps S3 to S5 are sequentially carried out for the same sample tube, it is preferable to analyze the surface roughness for another separate sample tube as in step S6. In step S6 of the present invention, the surface roughness for a certain area of the separate sample tube is analyzed to estimate the density of defects, and size and depth of a grain. It is preferable that the surface roughness analyzing step S6 be implemented using an atomic force microscope (AFM). By the fact that three points of the sample tube 100 are examined and analyzed using the AFM, the reliability of obtained data is enhanced, and a three-dimensional image of the inner surface of the sample tube, a surface roughness profile and a value of surface roughness can be determined from the final analysis data (see FIG. 3D).

Figure 4A:
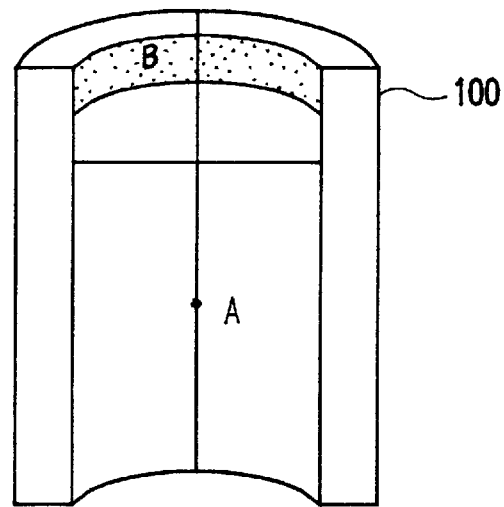
FIG. 4A is a cross-sectional view showing a gas tube which is to be estimated by the atomic force microscope (AFM) of FIG. 3D.
Figure 4B:
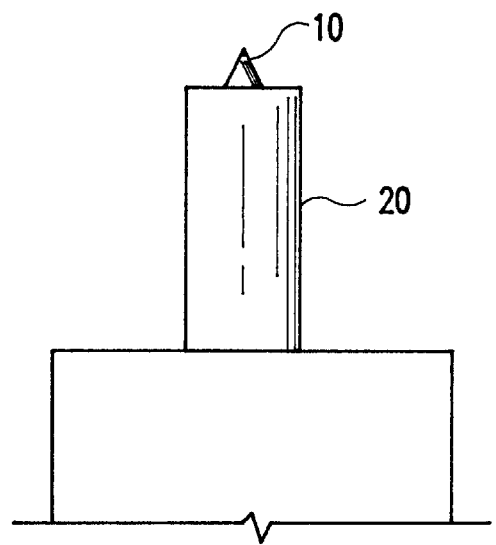
FIG. 4B is a front view of a tip holder of the atomic force microscope of the present invention.

The atomic force microscope (AFM) as shown in FIG. 4B includes a tip 10 which is contacted with the inner surface of the sample tube 100, and a tip holder 20 to which the tip 10 is securely fixed. According to the present invention, the tip holder 20 has a sufficiently small outer diameter and long length such that the tip 10 can easily approach the center point A of the sample tube 100 for measurement (see FIG. 4A). This overcomes a drawback of the prior art, where it is only possible to measure the surface point B on an outer edge of the sample tube 100 because the atomic force microscope (AFM) of the prior art has a large outer diameter and a short length. The surface point B cannot represent the whole sample tube 100 due to heat applied thereto during the cutting operation. Therefore, according to the atomic force microscope (AFM) of the present invention, it is possible to enlarge the measurable area to the center part of the sample tube 100, such that reliability in analyzing the surface roughness can be improved.

Finally, after steps S1 to S6 the sample tube 100 is synthetically analyzed in a synthetic analyzing step S7. Data for defect density and surface roughness, which are numerically expressed through the examining and analyzing steps, can easily be managed to afford precise estimation for the condition of the tubes.

As a result, the method and apparatus for estimating the performance of a gas tube provides some advantages in that it is possible to objectively analyze the initial state of a gas tube to define reference data which can be used in practice in the semiconductor manufacturing process.

In the drawings and specification, there have been disclosed typical preferred embodiments of the invention and, although specific terms are employed, they are used in a generic and descriptive sense only and not for purposes of limitation, the scope of the invention being set forth in the following claims.

What is claimed is:

1. A method for estimating the performance of a gas tube, the method comprising the steps of:
   (a) preparing a gas tube to be analyzed and cutting said gas tube in a desired size and shape to obtain a sample tube;
   (b) examining distribution of defects and surface condition of said cut sample tube with an optical microscope;
   (c) analyzing structural and compositional features of surface defects of said cut sample tube which can not be measured in said step (b), to determine type and composition of said surface defects and shape of a surface grain;
   (d) analyzing structure of an inner surface-treated layer of the sample tube along the thickness thereof; and
   (e) synthetically analyzing data for defect density and surface roughness, which are numerically expressed through said steps (a) to (d), to define a reference data which can be used in practicing a semiconductor manufacturing process.

2. A method for estimating the performance of a gas tube as claimed in claim 1, wherein said sample tube is made from stainless steel.

3. A method for estimating the performance of a gas tube as claimed in claim 1, wherein said step (c) is implemented using an electron-probe microscopy analyzer.

4. A method for estimating the performance of a gas tube as claimed in claim 1, wherein said step (d) is implemented using an Auger electron spectroscope.

5. A method for estimating the performance of a gas tube as claimed in claim 1, wherein said method further comprises the step of (f) analyzing a surface roughness over a predetermined area for estimating defect density, size and depth of a grain, and surface roughness of another sample tube.

6. A method for estimating the performance of a gas tube as claimed in claim 5, wherein said step (f) is implemented using an atomic force microscope.

* * * * *